(12) United States Patent
Smith

(10) Patent No.: US 9,615,778 B2
(45) Date of Patent: Apr. 11, 2017

(54) HEARING TEST PROBE

(71) Applicant: GN Otometrics A/S, Taastrup (DK)

(72) Inventor: Anders Smith, Hellerup (DK)

(73) Assignee: GN OTOMETRICS A/S, Taastrup (DK)

( * ) Notice: Subject to any disclaimer, the term of this patent is extended or adjusted under 35 U.S.C. 154(b) by 0 days.

(21) Appl. No.: 14/229,237

(22) Filed: Mar. 28, 2014

(65) Prior Publication Data

US 2015/0216452 A1    Aug. 6, 2015

(30) Foreign Application Priority Data

Feb. 4, 2014   (DK) .................................. 2014 00063

(51) Int. Cl.
*A61B 5/12*    (2006.01)
*A61B 5/00*    (2006.01)
*A61B 1/227*   (2006.01)

(52) U.S. Cl.
CPC .............. *A61B 5/126* (2013.01); *A61B 5/121* (2013.01); *A61B 5/6817* (2013.01); *A61B 1/2275* (2013.01)

(58) Field of Classification Search
None
See application file for complete search history.

(56) References Cited

U.S. PATENT DOCUMENTS

| | | | | |
|---|---|---|---|---|
| 2,118,523 A * | 5/1938 | Pitman | ........................... | 600/137 |
| 3,882,848 A * | 5/1975 | Klar et al. | ..................... | 600/559 |
| 4,057,051 A * | 11/1977 | Kerouac | ........................ | 600/559 |
| 4,993,424 A * | 2/1991 | Suszynski et al. | ........... | 600/549 |
| 5,018,872 A * | 5/1991 | Suszynski et al. | ........... | 374/133 |
| 5,063,946 A * | 11/1991 | Wada | ............................. | 600/559 |
| 5,445,158 A * | 8/1995 | Pompei | ......................... | 600/474 |
| 5,653,238 A * | 8/1997 | Pompei | ......................... | 600/474 |
| 5,738,633 A * | 4/1998 | Christiansen | ................. | 600/559 |
| 5,954,669 A * | 9/1999 | Iseberg | ......................... | 600/559 |
| 6,001,066 A * | 12/1999 | Canfield et al. | .............. | 600/559 |
| 6,047,205 A * | 4/2000 | Pompei | ......................... | 600/474 |
| 6,110,126 A * | 8/2000 | Zoth et al. | .................... | 600/559 |
| 6,149,605 A * | 11/2000 | Christiansen | ................. | 600/559 |
| 6,186,959 B1 * | 2/2001 | Canfield et al. | .............. | 600/559 |
| 6,219,573 B1 * | 4/2001 | Pompei | ......................... | 600/474 |
| 6,231,521 B1 * | 5/2001 | Zoth et al. | .................... | 600/559 |

(Continued)

FOREIGN PATENT DOCUMENTS

DE    10 2010 025 362 A1    12/2011

OTHER PUBLICATIONS

Extended European Search Report dated Mar. 20, 2015 for related European Patent Application No. 14162384.3, 6 pages.

(Continued)

*Primary Examiner* — Jermele M Hollington
*Assistant Examiner* — Suresh K Rajaputra
(74) *Attorney, Agent, or Firm* — Vista IP Law Group, LLP

(57) ABSTRACT

An apparatus for use in an audiologic test includes a probe extending along a longitudinal axis from a first end to a second end, the first end configured for insertion into an ear-canal of a person, the second end being opposite to the first end; wherein the probe comprises a probe part between the first end and the second end, the probe part having a first port; and wherein the probe further comprises a holder fixed to the probe part, the holder being configured to be held by an operator of the probe.

18 Claims, 6 Drawing Sheets

(56) References Cited

U.S. PATENT DOCUMENTS

| | | | |
|---|---|---|---|
| 6,299,584 B1* | 10/2001 | Iseberg | 600/559 |
| 6,702,758 B2* | 3/2004 | Iseberg | 600/559 |
| 7,268,466 B2* | 9/2007 | Rasmussen | 310/328 |
| 7,452,337 B2* | 11/2008 | Iseberg | 600/559 |
| 7,882,928 B2* | 2/2011 | McMahon et al. | 181/135 |
| 7,922,671 B2* | 4/2011 | Zoth et al. | 600/559 |
| 7,976,474 B2* | 7/2011 | Zoth et al. | 600/559 |
| 8,109,981 B2* | 2/2012 | Gertner et al. | 607/88 |
| 8,277,390 B2* | 10/2012 | Jennsen et al. | 600/559 |
| 8,419,655 B2* | 4/2013 | Birck | 600/559 |
| 9,055,924 B2* | 6/2015 | Roth | |
| 2010/0191144 A1 | 7/2010 | Zoth et al. | |
| 2012/0191004 A1* | 7/2012 | Iseberg et al. | 600/559 |
| 2013/0027515 A1* | 1/2013 | Vinther et al. | 348/44 |

OTHER PUBLICATIONS

First Technical Examination Report dated Oct. 15, 2014 for related Danish Patent Application No. PA 2014 70163, 5 pages.

\* cited by examiner

SECTION A-A

HEARING TEST PROBE

RELATED APPLICATION DATA

This application claims priority to and the benefit of Danish Patent Application No. PA 2014 00063, filed on Feb. 4, 2014, pending. The entire disclosure of the above application is expressly incorporated by reference herein.

FIELD

The present disclosure relates to a hearing test probe and the use of such a probe. In particular, the present disclosure relates to a probe used to perform an audiologic test, such as a tympanometric and/or an otoacoustic emission test.

BACKGROUND

In order to perform a tympanometric and/or an otoacoustic emission test, it is important that a probe entering the ear canal of a person to be tested is correctly positioned in the ear canal. Furthermore it is important that a suitable pressure is provided to the probe to ensure an air tight seal between the ear canal and the probe. Existing probes are difficult to handle in order to ensure correct positioning.

SUMMARY

Despite the known solutions there is still a need for probe for audiologic testing, which is easy to handle and easy to position correctly.

Accordingly, a probe for conducting an audiologic test is provided. The probe extends along a longitudinal axis from a first end to a second end, the first end configured (e.g., by having a certain size and/or shape) for insertion into an ear-canal of a person and the second end opposite to the first end, wherein the probe comprises a probe part between the first end and the second end, the probe part having a first port. The probe further comprises a holder fixed to the probe part. The holder is configured to be held by an operator of the probe, e.g. in a three-finger grip.

Also disclosed is a method of conducting an audiologic test. The method comprises inserting at least a part of a probe according to the probe disclosed herein in an ear-canal of a person. A device for performing the audiologic test is communicatively coupled to the probe via the first port of the probe.

It is an advantage of the disclosed probe that the probe provides for easy handling of the probe by an operator. The holder of the probe facilitates a three finger grip, such that an operator may grip the holder between his thumb and index finger and/or middle finger, while, at the same time, the operator is able to apply pressure to the probe using his thumb.

It is a further advantage of the probe that an operator of the probe is able to apply a pressure to the probe in a longitudinal direction of the probe. For example, the operator may apply pressure to the holder thereby easily pressing the probe into or against the ear canal of a person with a suitable force. Thereby, the operator may easily provide an air tight seal of the ear canal of the person and/or between the probe and the ear canal of the person.

An apparatus for use in an audiologic test is disclosed herein. The apparatus may include only a probe in some embodiments. In other embodiments, the apparatus may include the probe and an audiologic test device.

In some embodiments, the apparatus includes a probe extending along a longitudinal axis from a first end to a second end, the first end configured for insertion into an ear-canal of a person, the second end being opposite to the first end; wherein the probe comprises a probe part between the first end and the second end, the probe part having a first port; and wherein the probe further comprises a holder fixed to the probe part, the holder being configured to be held by an operator of the probe.

Optionally, the holder has a first cross-sectional dimension measured in a direction of a first axis perpendicular to the longitudinal axis, and wherein the first cross-sectional dimension is larger than a cross sectional dimension of the probe part measured in the direction of the first axis.

Optionally, the holder has a second cross-sectional dimension measured in a direction of a second axis perpendicular to the longitudinal axis, and wherein the second cross-sectional dimension is larger than a cross sectional dimension of the probe part measured in the direction of the second axis.

Optionally, the holder has a first surface facing the probe part, and wherein the first surface is a convex surface.

Optionally, a point of the first surface has a tangent plane with a normal, and wherein the normal and the longitudinal axis form an angle less than 45 degrees.

Optionally, the holder has a second surface facing away from the probe part, and wherein the second surface is a concave surface.

Optionally, the holder is configured for being held by the operator in a three-finger grip.

Optionally, the probe comprises a second port and a channel connecting the first port and the second port.

Optionally, the first port has a size sufficient to accommodate at least one tubular structure that comprises one or more electrical wires and/or air under pressure.

Optionally, the apparatus further includes a device for performing an audiologic test, wherein the probe is communicatively coupled to the device via the first port.

A method of conducting an audiologic test includes: inserting at least a part of a probe into an ear-canal of a person; wherein the probe extends along a longitudinal axis from a first end to a second end, the first end configured for insertion into an ear-canal of a person, the second end being opposite to the first end; wherein the probe comprises a probe part between the first end and the second end, the probe part having a first port; and wherein the probe further comprises a holder fixed to the probe part, the holder being configured to be held by an operator of the probe.

Optionally, the method further includes communicatively coupling the probe with an audiologic test device via the first port.

Other aspects and features will be evident from reading the following detailed description.

BRIEF DESCRIPTION OF THE DRAWINGS

In the following, preferred embodiments of the new hearing instrument are explained in more detail with reference to the drawing, wherein.

DETAILED DESCRIPTION

Figure 1:
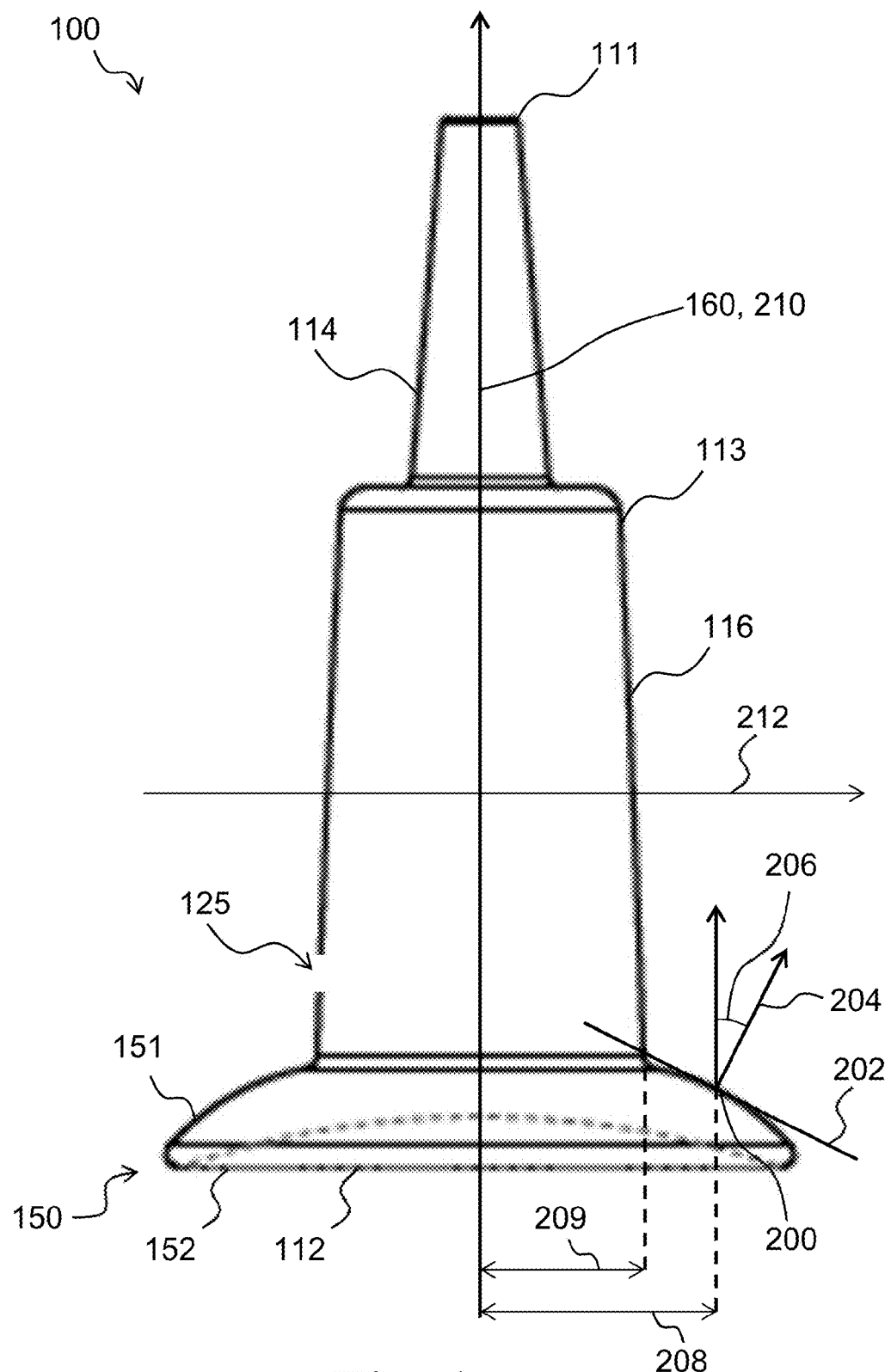
FIG. 1 schematically illustrates a side view of an exemplary hearing test probe

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The probe has a first end and the first end may be an end of a section, such as a first section, of the probe part.

The probe part may have a plurality of ports, such as the first port and a second port and/or a third port.

The part of the probe for insertion into the ear-canal of the person for conducting an audiologic test may be a section of the probe part, such as the first section of the probe part.

The holder may be fixed on or near the second end of the probe, e.g. within 2 cm from the second end, such as within 1 cm from the second end, such as within 0.5 cm. from the second end, such as within 0.2 cm. from the second end.

The holder may have a first cross-sectional dimension (e.g., a first holder-diameter) measured along a first axis perpendicular to the longitudinal axis. The first cross-sectional dimension may be larger than a cross-sectional dimension (e.g., diameter) of the probe part (e.g., measured along a direction of the first axis). For example, the difference between the maximum probe part diameter and the first holder-diameter may be at least 5 mm.

The holder may have a second cross-sectional dimension (e.g., a second holder-diameter) measured along a second axis perpendicular to the longitudinal axis. The second cross-sectional dimension may be larger than a cross-sectional dimension (e.g., a diameter) of the probe part (e.g., measured along a direction of the second axis). For example, the difference between the maximum probe part cross-sectional dimension and the second holder cross-sectional dimension may be at least 5 mm.

A cross-sectional dimension (e.g., a diameter), such as the first holder cross-sectional dimension and/or the second holder cross-sectional dimension, may be defined as the largest straight distance between two points on the perimeter of the form. For example, the first holder cross-sectional dimension may be the largest distance along the first axis between two points on the perimeter of the holder. Similarly, the second holder cross-sectional dimension may be the largest distance along the second axis between two points on the perimeter of the holder.

The first axis and the second axis may form an angle larger than 30 degrees, such as larger than 40 degrees, such as larger than 60 degrees. The first axis and the second axis may be perpendicular.

The probe, the probe part and/or the holder may have a circular or a non-circular cross section perpendicular to the longitudinal axis of the probe, such as an oval, polygonal, rectangular, polygonal with rounded corners, etc.

Providing the probe, the probe part, and/or the holder, with a non-circular cross section may allow easy twisting of the probe.

The holder may have a holder cross-sectional dimension (e.g., diameter), D2 measured in a direction perpendicular to the longitudinal axis of the probe, e.g. along the first axis (first holder cross-sectional dimension) or a second axis (second holder cross-sectional dimension). The probe part may have a probe cross-sectional dimension (e.g., diameter) D1 in a direction perpendicular to the longitudinal axis, e.g. measured along a direction of the first axis or the second axis. D2 may be greater than D2. For example, D2 may be of the order 40 mm, e.g. 25-45 mm, such as 30-35 mm, and D1 may be of the average ear canal cross-sectional dimension (e.g., diameter), e.g. 5-15 mm. D1 and D2 may be along the same axis, such as the first axis or the second axis.

The size and/or shape of different cross-sections of the probe, the holder and/or probe part perpendicular to the longitudinal axis taken at different positions along the longitudinal axis may vary. For example, the probe may have a first section having a first cross section perpendicular to the longitudinal axis of the probe, and a second section having a second cross section perpendicular to the longitudinal axis of the probe. The first cross section and the second cross section may be different in size and/or shape.

Additionally or alternatively, a first cross-section of the holder at a first position along the longitudinal axis may have a different size and/or shape than a second cross-section of the holder at a second position along the longitudinal axis, the first position being different from the second position.

The holder may have a first surface. The holder may further have a second surface opposite the first surface. The first surface may face the probe part. The second surface may face away from the probe part. The holder may be fixed to the probe part by the first surface, i.e. the first surface and a part of the probe part may be joined together.

The first port may be located at least 5 mm from the first surface along the longitudinal axis, such as at least 7 mm, such as at least 10 mm. Providing a minimum space between the first port and the first surface may allow the operator to place a finger, such as the index finger or the middle finger, on the first surface without obstructing the first port.

The first surface may be a convex surface. The second surface may be a concave surface. The holder may be configured for being held by the operator in a three-finger grip, e.g. by an operator placing the index finger and the middle finger on the first surface on each side of the probe part, and the thumb on the second holder-surface.

A first point of the first surface may have a first tangent plane with a first normal. The first normal and the longitudinal axis may form an angle less than 45 degrees, such as less than 35 degrees, such as less than 30 degrees. The first point may be located at a first distance from a center axis of the probe. The first distance may be larger than a first threshold. The first threshold may be at least 4 mm, such as 6 mm or 8 mm. Alternatively, the first distance may be larger than the distance from the center axis to a point on the perimeter of a cross-section of the probe part perpendicular to the longitudinal axis, such as a cross-section of the probe part proximal to the second end, such as a cross-section of the probe part between the second end and 1 cm from the second end along the longitudinal axis.

The angle between the longitudinal axis and the first normal being less than 45 degrees, or less than 35 degrees, or less than 30 degrees, has the effect, that the holder has a surface, e.g. the first surface which is approximately perpendicular to the longitudinal axis. This provides a surface, e.g. the first surface, for placing the index and/or middle finger, when handling the probe, such as handling the probe with a three finger grip.

The probe part may comprise a first section. The first section may be configured for hermetically sealing the ear-canal of the person. Alternatively or additionally, the first section may be configured for engagement with a tip. The tip may be configured to hermetically seal the ear-canal of the person, at least during the audiologic test. The tip may be chosen from a plurality of tips with different sizes and/or properties to accommodate different ear and/or ear-canal sizes. The tip may be flexible. For example, the tip may be made of a flexible material, e.g. a thermoplastic elastomer, a rubber etc. The tip may be replaceable and/or disposable. A disposable tip may prevent requirement of sterilizing the probe because the disposable tip may be sterile and disposed of after use. A replaceable tip facilitates adaption of the test probe for different ear canal geometries/sizes.

The holder may be fixed to the probe part using fixation means. Fixation means may be any one or more of a click lock, a twist on lock, a screw, a press-fit lock, glue, bayonet-clutch etc.

The probe part and the holder may be cast together. Casting the probe part and the holder together may improve durability of the probe. Additionally or alternatively, casting the probe part and the holder together may lower manufacturing costs. However, providing a holder which is separable from the probe part, may allow a holder which is attachable to conventional test probes.

The holder may be cast in the same material as the probe part. Casting the probe part and the holder in same materials may incur lower manufacturing costs. Alternatively, the holder may be cast in a different material than the probe part. Different materials may provide different desirable properties such as flexibility, opacity, rigidity, durability etc.

The holder and the probe part may exhibit different mechanical properties such as flexibility, rigidity, durability etc. Different mechanical properties may be acquired for example by varying the material and/or thickness of parts. The holder may be made from a material that is more flexible than the material of the probe part. The thickness of the holder may be such that the holder is more flexible than the probe part.

The holder and the probe part may exhibit different visual properties such as colour, opacity, reflection, etc. Different visual properties may be realized for example by making the holder and the probe part in different materials and/or thickness. For example, the holder may be transparent or substantially transparent.

The first port may be configured to accommodate at least one tubular input (tubular structure). The at least one tubular input may be configured to accommodate an electrical wire e.g. a first wire and/or a second wire. The at least one tubular input may be configured to accommodate air under pressure.

The probe may comprise a second port. The probe may comprise a channel connecting the first port and the second port. The channel may be formed in the probe part. The channel may allow fluid communication between the first port and the second port. For example, the probe part may be substantially tubular. The probe part may taper having a smaller cross-sectional dimension (e.g., a smaller diameter) towards the first end. Alternatively or additionally, the probe part may comprise a tube extending from the first port to the second port.

The first port may be connectable to a tubular member. The tubular member may comprise a tube and/or a wire, or a tube containing a wire or a double tube, wherein a first tube of the double tube contains a wire or a cable and a second tube of the double tube is configured to accommodate a fluid such as air. The first port may be connectable to a first end of the tubular member. A second end of the tubular member may be connectable to a device for performing an audiologic test. The device may be configured for pumping a fluid such as atmospheric air into the ear canal in order to increase/decrease pressure against the tympanic membrane, e.g. the device may pump fluid into the ear canal via the tubular member and the channel extending from the first port to the second port.

The probe part may accommodate a receiver (loudspeaker), such as a first and/or second receiver. The receiver may be connectable to an electrical wire, e.g. the first wire. The receiver may be connectable to a device configured for performing an audiologic test, e.g. via an electrical wire, such as the first wire.

The probe part may accommodate a microphone, such as a first microphone and/or a second microphone. The microphone may be connectable to an electrical wire, e.g. the second wire. The microphone may be connectable to a device configured for performing an audiologic test, e.g. via an electrical wire, such as the second wire.

The audiologic test to be performed may be chosen from a group consisting of tympanometric test and otoacoustic emission test.

The operator and the person, as described, may be two individuals. However, the operator and the person may be the same person.

FIG. 1 schematically illustrates a side view of an exemplary probe 100 for conducting an audiologic test. The probe 100 comprises a first end 111 and a second end 112. The probe 100 further comprises a probe part 113 between the first end 111 and the second end 112. The probe 100 further comprises a first port 125.

The probe 100 extends along a longitudinal axis 160. The probe part 113 has a first section 114 and a second section 116.

The probe 100 further comprises a holder 150. The holder 150 has a first surface 151 and a second holder surface 152. The second holder surface 152 being opposite the first surface 151. The holder 150 is attached to the probe part 113 proximal to the second end 112. The first surface 151 is facing the probe part 113 and the second holder surface 152 is facing away from the probe part.

A first point 200 of the first surface 151 has a first tangent plane 202 with a first normal 204. The first normal 204 and the longitudinal axis 160 form an angle 206 less than 45 degrees. As illustrated in FIG. 1 the angle 206 is approximately 30 degrees. In other exemplary probes, the angle 206 may be between 0-20 degrees.

In the depicted example, the first point is located at a first distance 208 along a first axis 212. The first axis 212 is perpendicular to the longitudinal axis 160. The first distance 208 is larger than a second distance 209 along the first axis 212. The first distance 208 is the distance between a center axis 210 and the first point 200. The second distance 209 is the distance between the center axis 210 and a point on the perimeter of the probe part 113 proximal to the second end 112, such as less than 2 cm from the first point along the longitudinal axis 160. The first distance 208 may be larger than the second distance 209, such as at least 2 mm larger than the second distance 209, such as at least 4 mm larger than the second distance.

The holder 150 is configured (e.g., by having certain size and/or shape) to allow an operator using the probe 100 to utilize a three-finger-grip, wherein the thumb is positioned on the second holder surface 152, and the index and middle finger are positioned against the first surface 151 on either side of the probe part 113. The operator may thus be permitted to apply pressure to the probe 100 in a longitudinal direction of the probe 100, i.e. towards a person's ear canal.

To provide for a comfortable and firm grip on the probe 100, the second holder surface 152 may be concave, as shown in FIG. 1. The first surface 151 may be convex as shown in FIG. 1.

Figure 2:
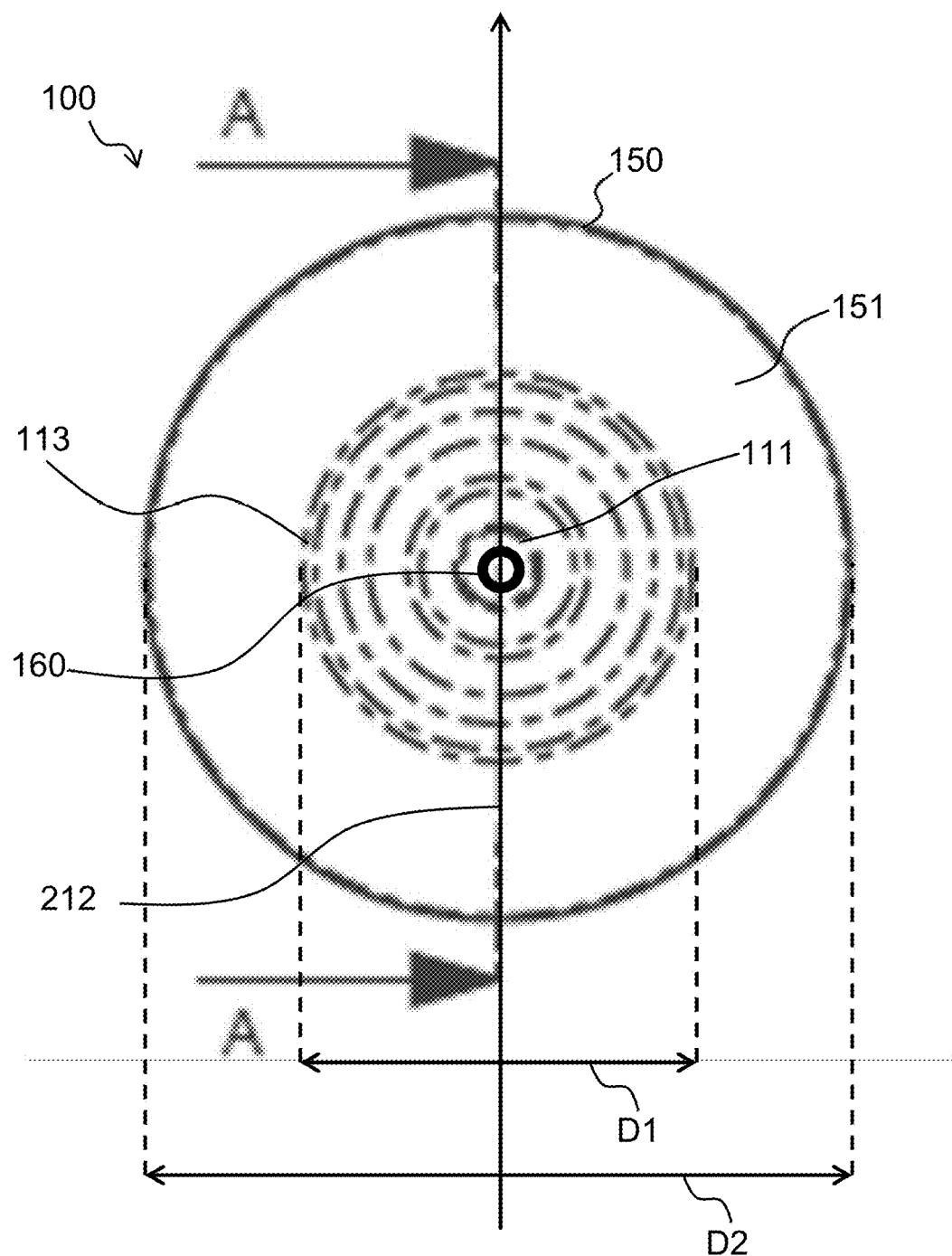
FIG. 2 schematically illustrates a front view of an exemplary hearing test probe FIG. 3 schematically illustrates a cross section of an exemplary hearing test probe FIG. 4 a)-d) schematically illustrates end views of exemplary hearing test probes FIG. 5 schematically illustrates an exemplary system comprising an exemplary probe FIG. 6 schematically illustrates an exemplary system comprising an exemplary probe

FIG. 2 schematically illustrates a front view of an exemplary hearing probe 100. FIG. 2 furthermore illustrates an exemplary circular shape of the holder 150 and circular shape of the probe part 113. Alternatively, the shape of the holder 150 and/or probe part 113 may be triangular, rectangular, oval, etc. The probe part 113 and the holder 150 may have different shapes. A cross-section of the probe part 113 may vary along the longitudinal axis. For example, the probe part 113 may have a circular cross-sectional shape proximal to the first end 111, and the probe part 113 may have an oval or polygonal shape proximal to the second end 112.

The holder 150 may be symmetrical about an axis perpendicular to the longitudinal axis, such as the first axis 212 or a second axis.

In the depicted example, the probe part 113 has a probe cross-sectional dimension (e.g., diameter) D1, and the holder has a holder cross-sectional dimension (e.g., diameter) D2. The cross-sectional dimensions D1, D2 may be defined as the largest straight distance between two points on the perimeter of a cross-section perpendicular to the longitudinal axis. The probe cross-sectional dimension D1 may vary along the longitudinal axis. The probe cross-sectional dimension D1 may be smaller proximal to the first end 111 than proximal to the second end 112. The probe cross-sectional dimension D1 may be smallest at the first end 111.

Figure 3:
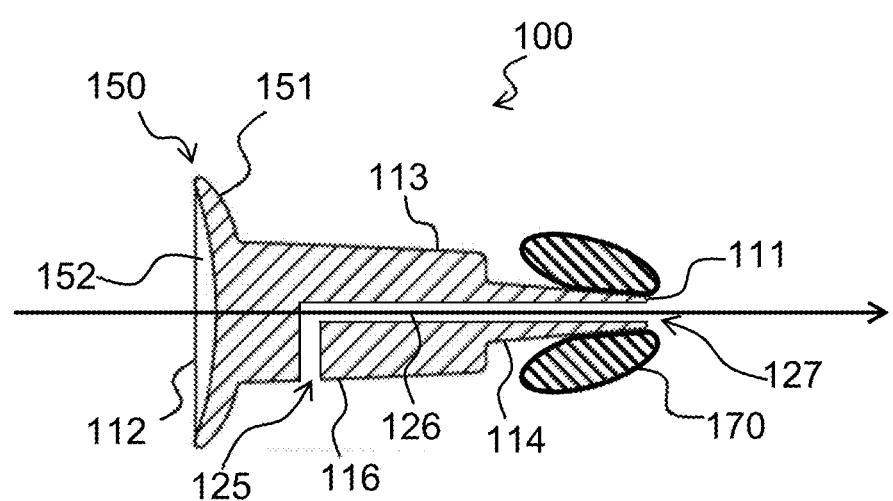

FIG. 3 schematically illustrates a cross section of an exemplary hearing test probe 100 along the longitudinal axis. The cross section A-A shown in FIG. 3 is the cross section as indicated on FIG. 2. The probe part 113 has a first section 114 and a second section 116. The first section 114 is proximal to the first end 111, and the second section 116 is proximal to the second end 112.

The probe 100 comprises a probe channel 126 extending from the first port 125 to a second port 127. The second port 127 is located at the first end 111. The probe channel 126 and the second port 127 allows fluid communication between the first port 125 and the ear canal of the person, when a part of the probe 100 is inserted into the person's ear canal. The probe channel 126 depicted consists of straight parts, however, the probe channel 126 may just as well be curved and/or have curved parts.

In the depicted example, the first port 125 is formed in the second section 116, and the second port 127 is formed in the first section 114. Alternatively, the first port 125 and the second port 127 may be formed in the same section, e.g. the first section 114.

The first section 114 is configured to accommodate a disposable and/or flexible tip 170. The tip 170 may be fitted onto the first section 114 in order to ensure a tight fit of the first end 111 in an ear canal. Furthermore, a disposable tip 170 may prevent requirement of sterilizing the probe 100 after use.

Figure 4:
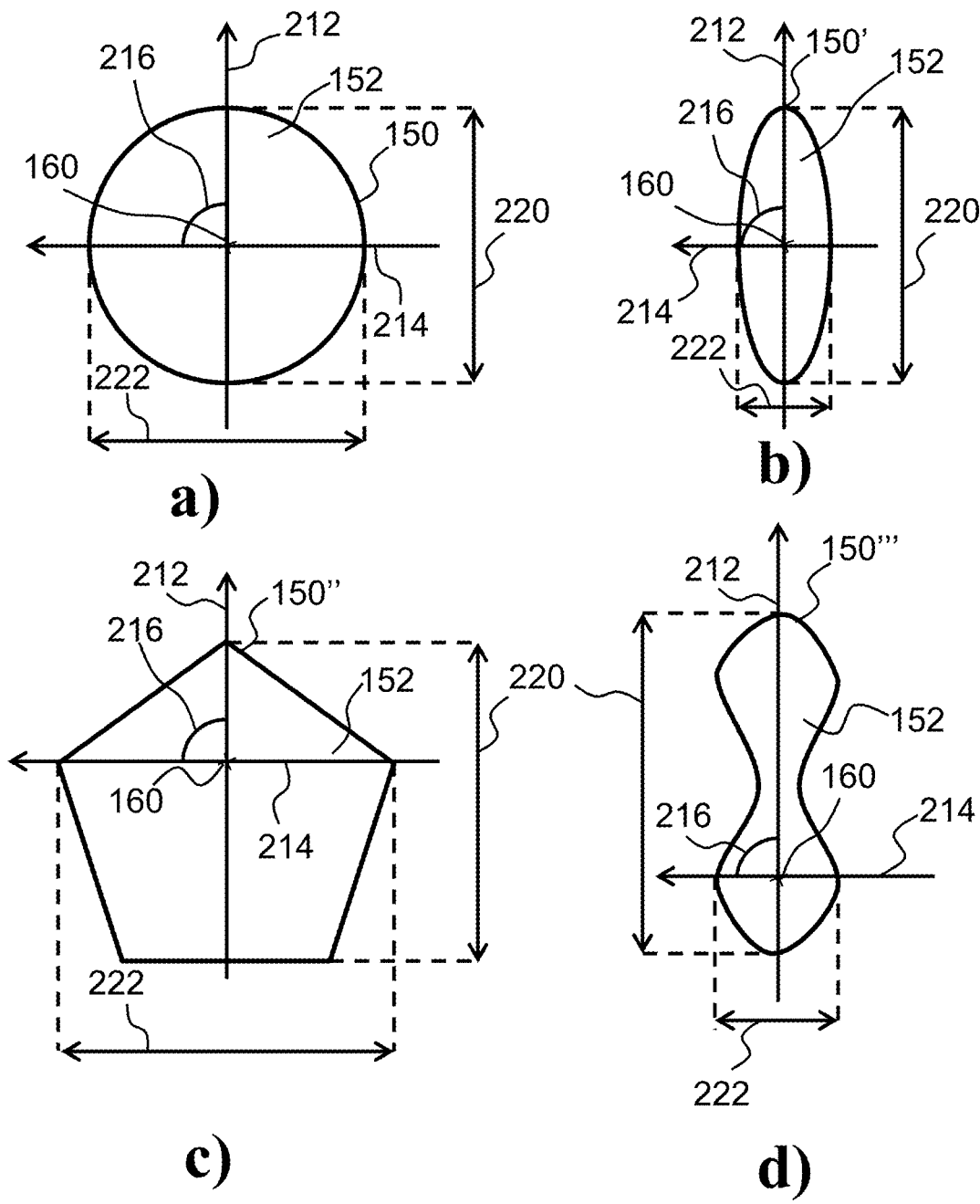

FIGS. 4a-d schematically illustrates exemplary shapes of a holder 150 seen from end views. FIGS. 4a-b shows the holder 150, 150', 150", 150''' having a first holder cross-sectional dimension (e.g., diameter) 220 along a first axis 212. The first axis 212 is perpendicular to the longitudinal axis 160. The holder 150, 150', 150", 150''' has a second holder cross-sectional dimension (e.g., diameter) 222 along a second axis 214. The second axis 214 is perpendicular to the longitudinal axis 160. In FIGS. 4a-d the first axis 212 and the second axis 214 are perpendicular, i.e. the angle 216 formed by the first 212 and the second axis 214 is 90 degrees. The angle 216 formed by the first 212 and the second axis 214 may be more than 30 degrees, such as more than 45 degrees, such as more than 60 degrees, such as more than 75 degrees, such as 90 degrees.

The first holder cross-sectional dimension 220 and/or the second holder cross-sectional dimension 222 may be in the range between 25-100 mm, such as in the range between 30-70 mm, such as 40 mm.

FIG. 4a schematically illustrates an exemplary holder 150 having a circular shape with the same first holder cross-sectional dimension 220 and second holder cross-sectional dimension 222 of about 25 mm.

FIG. 4b schematically illustrates an exemplary holder 150' having an oval shape. The first holder cross-sectional dimension 220 and the second holder cross-sectional dimension 222 are different. The first holder cross-sectional dimension 220 is in FIG. 4b larger than the second holder cross-sectional dimension 222. The second holder cross-sectional dimension may be half of the first holder cross-sectional dimension, or less than ⅓ of the first holder cross-sectional dimension, or less than half of the first holder cross-sectional dimension. The first holder cross-sectional dimension may be 50 mm and the second holder cross-sectional dimension may be 25 mm. The smallest of the first and second holder cross-sectional dimension, e.g. the second holder cross-sectional dimension, may be the same or substantially the same cross-sectional dimension as a cross-sectional dimension of the probe part.

FIG. 4c schematically illustrates an exemplary holder 150" having a polygonal shape. The specifically depicted exemplary holder 150" has a pentagonal shape. The first holder cross-sectional dimension 220 and the second holder cross-sectional dimension 222 are in FIG. 4c different. The second holder cross-sectional dimension 222 is in FIG. 4c larger than the first holder cross-sectional dimension 220.

FIG. 4d schematically illustrates an exemplary holder 150''' having an arbitrary shape. The first holder cross-sectional dimension 220 and the second holder cross-sectional dimension 222 are the greatest distance along a straight line parallel to the respective first and second axis between two points on the perimeter of the holder 150'''. The first holder cross-sectional dimension 220 and the second holder cross-sectional dimension 222 are in FIG. 4d different. The first holder cross-sectional dimension 220 is in FIG. 4d larger than the second holder cross-sectional dimension 222.

Figure 5:
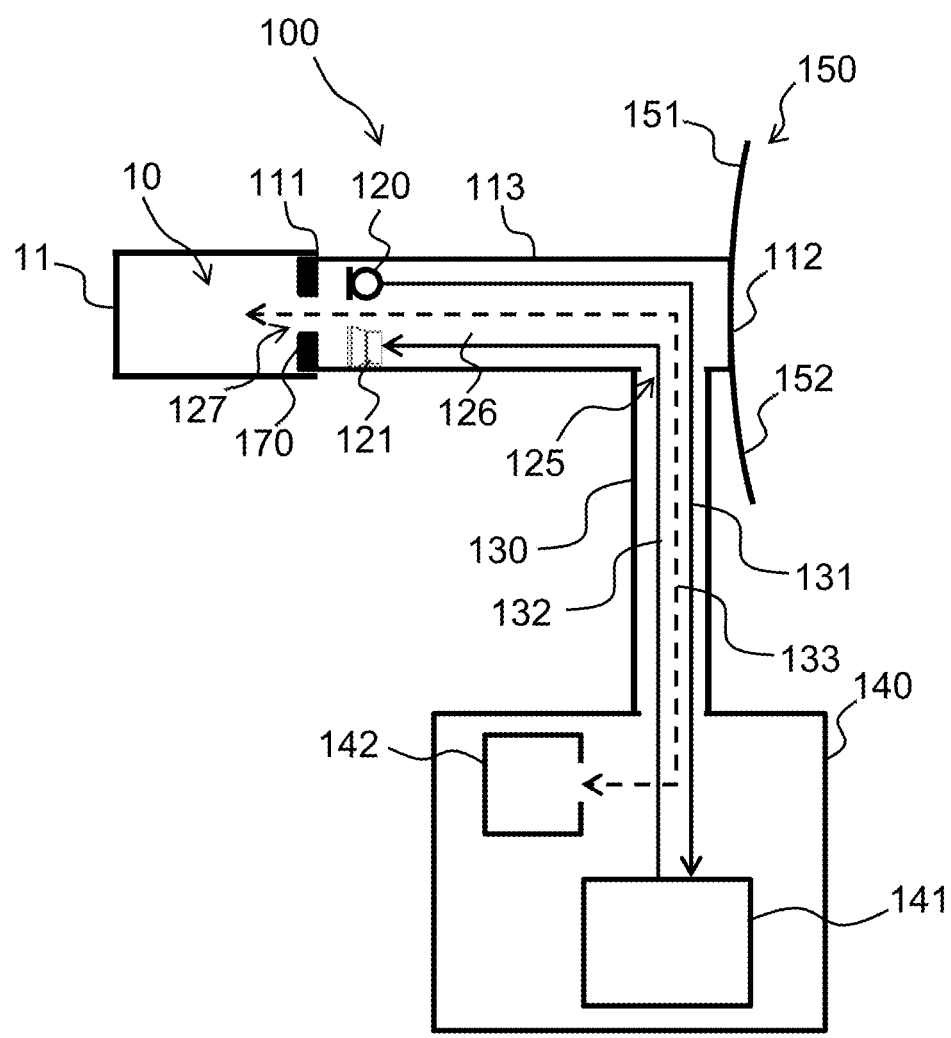

FIG. 5 schematically illustrates an exemplary system comprising an exemplary probe 100 and an exemplary device 140 for performing an audiologic test. The probe 100 is inserted into a person's ear canal 10. The ear canal 10 comprises a tympanic membrane 11.

The probe 100 comprises a microphone 120. The microphone 120 is adapted to record a first audio signal. For example, the microphone 120 may be configured for recording an audio signal, e.g. the first audio signal, reflected from the tympanic membrane 11.

The probe 100 comprises a receiver (loudspeaker) 121. The receiver 121 is adapted to transmit a second audio signal. For example, the receiver 121 may be configured for transmitting an audio signal, e.g. the second audio signal, towards the tympanic membrane 11.

The first port 125 may be coupled to the device 140 by a tubular member 130. The tubular member 130 may comprise a tube or a wire, or a tube containing a wire, or a double tube, wherein a first tube of the double tube contains a wire and a second tube of the double tube is configured to accommodate a fluid. The tubular member 130 may comprise a tube wherein a wire, or a plurality of wires, is cast in the wall of the tubular member 130. The wire(s) may electrically connect the receiver 121 and/or the microphone 120 with the device 140.

The device 140 may comprise a processing unit 141. The processing unit 141 may be communicatively coupled to the microphone 120 via a first wire 131 contained in the tubular member 130 The processing unit 141 may be communicatively coupled to the receiver 121 via a second wire 132 contained in the tubular member 130.

The device 140 may comprise a pump 142. The pump 142 may be in fluid communication 133 with the ear canal 10 via the tubular member 130, the first port 125, the probe channel 126, and the second port 127. Hence, the device 140 may be able to pump fluid, such as atmospheric air, into the ear canal in order to increase pressure against the tympanic membrane. Alternatively or additionally, the device 140 may be able to remove fluid, such as atmospheric air, from the ear canal in order to decrease pressure against the tympanic membrane.

The receiver 121 and/or the microphone 120 may be positioned distal to the first end 111, e.g. in the tubular member 130 proximal to the first port 125, and acoustic signals may be conducted between the ear canal 10 and the receiver 121 and/or the microphone 120 via the channel 126 and second port 127.

Figure 6:
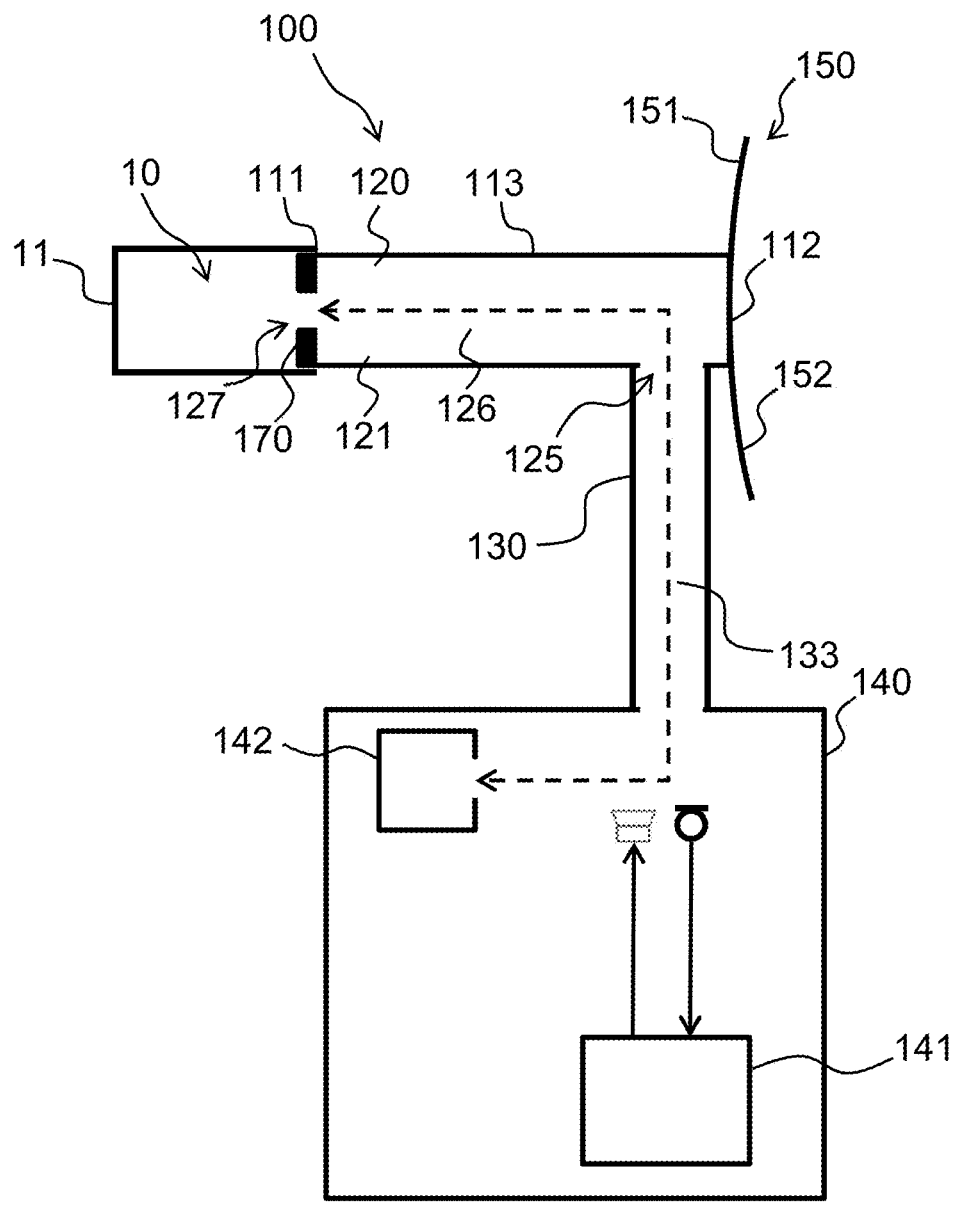

FIG. 6 schematically illustrates another exemplary system comprising an exemplary probe 100 and an exemplary device 140 for performing an audiologic test. The exemplary system depicted in FIG. 6 comprises the same features as the system depicted in FIG. 6. However, the system in FIG. 6 illustrates a system wherein the microphone 120 and the receiver 121 are contained in the device 140. Acoustic signals between the ear canal 10 and the receiver 121 and/or the microphone 120 is transmitted through the tubular member 130, the first port 125, the channel 126, and the second port 127.

Embodiments and aspects are disclosed in the following items:

Item 1. A probe for conducting an audiologic test, the probe extending along a longitudinal axis from a first end to a second end, the first end configured for insertion into an ear-canal of a person and the second end opposite to the first end, wherein the probe comprises a probe part between the first end and the second end; wherein the probe part has a first port; and wherein the probe further comprises a holder fixed to the probe part, the holder being configured to being held by an operator of the probe.

Item 2. Probe according to item 1, wherein the holder has a first holder cross-sectional dimension along a first axis perpendicular to the longitudinal axis, wherein the first holder cross-sectional dimension is larger than a cross-sectional dimension of the probe part along a direction of the first axis.

Item 3. Probe according to item 2, wherein the holder has a second holder cross-sectional dimension along a second axis perpendicular to the longitudinal axis, wherein the second holder cross-sectional dimension is larger than a cross-sectional dimension of the probe part along a direction of the second axis.

Item 4. Probe according to item 3, wherein the first axis and the second axis form an angle larger than 30 degrees.

Item 5. Probe according to any of items 1-4, wherein the holder has a first surface facing the probe part.

Item 6. Probe according to item 5, wherein the first surface is a convex surface.

Item 7. Probe according to any of items 5-6, wherein a first point of the first surface has a first tangent plane with a first normal, and wherein the first normal and the longitudinal axis form an angle less than 45 degrees.

Item 8. Probe according to item 7, wherein the first point is located at a first distance from a center axis of the probe, the first distance being larger than a first threshold, such as 4 mm.

Item 9. Probe according to any of items 1-8, wherein the holder has a second surface facing away from the probe part, wherein the second surface is a concave surface.

Item 10. The probe according to any of items 1-9, wherein the probe part comprises a first section configured for engagement with a tip for hermetically sealing the ear-canal of the person during the audiologic test.

Item 11. The probe according to any of items 1-10, wherein the holder is configured for being held by the operator in a three-finger grip.

Item 12. The probe according to any of items 1-11, wherein the probe comprises a second port and a channel connecting the first port and the second port.

Item 13. The probe according to any of items 1-12, wherein the first port is configured to accommodate at least one tubular input configured to accommodate one or more electrical wires and/or air under pressure.

Item 14. The probe according to any of items 1-13, wherein the audiologic test to be performed is chosen from the group consisting of tympanometric test and otoacoustic emission test.

Item 15. A method of conducting an audiologic test, wherein the method comprises inserting at least a part of a probe according to anyone of items 1 to 14 into an ear-canal of a person, wherein a device for performing the audiologic test is communicatively coupled to the probe via the first port.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

LIST OF REFERENCES 10 ear canal
11 tympanic membrane
100 probe
111 first end
112 second end
113 probe part
114 first section
116 second section
120 microphone
121 receiver
125 first port
126 probe channel
127 second port 130 tubular member
131 first wire
132 second wire
133 fluid communication
140 device
141 processing unit
142 pump
150 holder
151 first surface
152 second surface
160 longitudinal axis
170 tip
200 first point
202 first tangent plane
204 first normal
206 angle formed by longitudinal axis and first normal
208 first distance
209 second distance
210 center axis
212 first axis
214 second axis
216 angle formed by first and second axis
220 first holder cross-sectional dimension
222 second holder cross-sectional dimension
$D_1$ probe cross-sectional dimension
$D_2$ holder cross-sectional dimension

The invention claimed is:

1. An apparatus for use in an audiologic test, comprising:
a probe having a first end and a second end, the probe extending along a longitudinal axis between a first end and a second end, the first end configured for insertion into an ear-canal of a person, the second end being opposite to the first end;
wherein the probe comprises a probe part between the first end and the second end, the probe part having a first port, wherein the first port is located at an exterior surface at a transverse side of the probe part;
wherein the probe further comprises a holder located at a position along the longitudinal axis, the holder being configured to be held by an operator of the probe and being different from the probe part with the first port.

2. The apparatus according to claim 1, wherein the holder has a first cross-sectional dimension measured in a direction of a first axis perpendicular to the longitudinal axis, and wherein the first cross-sectional dimension is larger than a cross sectional dimension of the probe part measured in the direction of the first axis.

3. The apparatus according to claim 2, wherein the holder has a second cross-sectional dimension measured in a direction of a second axis perpendicular to the longitudinal axis, and wherein the second cross-sectional dimension is larger than a cross sectional dimension of the probe part measured in the direction of the second axis.

4. An apparatus for use in an audiologic test, comprising:
a probe having a first end and a second end, the probe extending along a longitudinal axis between a first end and a second end, the first end configured for insertion into an ear-canal of a person, the second end being opposite to the first end;
wherein the probe comprises a probe part between the first end and the second end, the probe part having a first port;
wherein the probe further comprises a holder located at a position along the longitudinal axis, the holder being configured to be held by an operator of the probe; and
wherein the holder has a first surface facing the probe part, and wherein the first surface is a convex surface.

5. The apparatus according to claim 4, wherein a point of the first surface has a tangent plane with a normal, and wherein the normal and the longitudinal axis form an angle less than 45 degrees.

6. The apparatus according to claim 4, wherein the holder has a second surface facing away from the probe part, and wherein the second surface is a concave surface.

7. An apparatus for use in an audiologic test, comprising:
a probe having a first end and a second end, the probe extending along a longitudinal axis between a first end and a second end, the first end configured for insertion into an ear-canal of a person, the second end being opposite to the first end;
wherein the probe comprises a probe part between the first end and the second end, the probe part having a first port;
wherein the probe further comprises a holder configured to be held by an operator of the probe; and
wherein the holder is configured for being held by the operator in a three-finger grip.

8. The apparatus according to claim 1, wherein the probe comprises a second port and a channel connecting the first port and the second port.

9. The apparatus according to claim 1, wherein the first port has a size sufficient to accommodate at least one tubular structure that comprises one or more electrical wires and/or air under pressure.

10. The apparatus according to claim 1, further comprising a device for performing an audiologic test, wherein the probe is communicatively coupled to the device via the first port.

11. A method of conducting an audiologic test, comprising:
inserting at least a part of a probe into an ear-canal of a person;
wherein the probe extends along a longitudinal axis from a first end to a second end, the first end configured for insertion into an ear-canal of a person, the second end being opposite to the first end;
wherein the probe comprises a probe part between the first end and the second end, the probe part having a first port; and
wherein the probe further comprises a holder located at a position along the longitudinal axis, the holder being configured to be held by an operator of the probe and being different from the probe part with the first port.

12. The method of claim 11, further comprising communicatively coupling the probe with an audiologic test device via the first port.

13. The method of claim 11, wherein the holder is at the second end that is opposite to the first end of the probe.

14. The apparatus of claim 1, wherein the first port is located at an exterior surface at a transverse side of the probe part.

15. The apparatus of claim 1, wherein the holder is at the second end that is opposite to the first end of the probe.

16. An apparatus for use in an audiologic test, comprising:
a probe having a first end and a second end, the probe extending along a longitudinal axis between a first end and a second end, the first end configured for insertion into an ear-canal of a person, the second end being opposite to the first end;
wherein the probe comprises a probe part between the first end and the second end, the probe part having a first port located at an exterior surface at a transverse side of the probe part; and wherein the probe further comprises a holder, the holder being configured to be held by an operator of the probe and being different from the probe part with the first port.

17. The apparatus of claim 1, wherein the holder is proximal to the probe part that has the transverse side with the first port.

18. The apparatus of claim 1, wherein the holder has a cross sectional dimension that is larger than a cross sectional dimension of the probe part having the transverse side with the first port.

* * * * *